US00PP29684P3

(12) United States Plant Patent
Hansen

(10) Patent No.: US PP29,684 P3
(45) Date of Patent: Sep. 18, 2018

(54) ***DIANTHUS* PLANT NAMED 'CHERRY VANILLA'**

(50) Latin Name: ***Dianthus* hybrid**
Varietal Denomination: Cherry Vanilla

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/530,507

(22) Filed: Jan. 23, 2017

(65) Prior Publication Data

US 2018/0213703 P1 Jul. 26, 2018

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273, 278, 277, 283, 272
CPC ..... A01H 5/0233; A01H 5/02; A01H 5/00; A01H 6/305; A01H 6/30
See application file for complete search history.

(56) References Cited

U.S. PATENT DOCUMENTS

PP13,915 P2 * 6/2003 Whetman ..... A01H 5/0233 Plt./279

* cited by examiner

*Primary Examiner* — June Hwu

(57) ABSTRACT

A new and unique plant cultivar of perennial carnation or pinks, *Dianthus* plant named 'Cherry Vanilla' with numerous, large, fully-double, lightly-fragrant flowers producing a rounded full face of velvety-red flowers. The flowers cover top to bottom of clump on well-branched stems having up to 4 flowers per stem. Petals have fine serrations, a velvety red coloration with fine speckling and margin of light pink. The plant is compact with long, thin, grey-green foliage.

1 Drawing Sheet

Botanical denomination: *Dianthus* hybrid.
Cultivar designation: 'Cherry Vanilla'.

BACKGROUND OF THE INVENTION

The present invention relates to the new and distinct cultivar of carnation or pinks from the genus *Dianthus* and given the cultivar name 'Cherry Vanilla'. The new plant was the result of an intentional cross on May 14, 2012 under the direction of the inventor between *Dianthus* 'WP Passion' U.S. Plant Pat. No. 20,440 as the female or seed parent and 'Valda Isolde' U.S. Plant Pat. No. 13,915 (known by the tradename of Fancy Kickers) as the male or pollen parent. The cross was harvested and sown on Jul. 2, 2012. The new hybrid was first isolated from trials at a wholesale perennial nursery in Zeeland, Mich. during the summer of 2013 as a single seedling clone and given the breeder number 12-64-1 later in the evaluation processes. *Dianthus* 'Cherry Vanilla' has been asexually propagated at the same nursery in Zeeland, Mich. since 2013 using traditional shoot tip cutting procedures and found to reproduce plants that are identical and exhibit all the characteristics of the original plant.

No plants of *Dianthus* 'Cherry Vanilla' have been sold in this country, or anywhere in the world, under this or any name, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

*Dianthus* 'Cherry Vanilla' has not been evaluated under all possible environmental conditions. The phenotype may vary with variations in environment including: growing temperature, available sunlight, nutrients, water, etc. without a change in the genotype of the plant.

Compared to the new plant, the female parent, 'WP Passion', the new plant has deep red flowers with a light pink picotee petal margin rather than solid red. Compared with 'Cherry Vanilla', the male parent, 'Fancy Knickers', has nearly solid white flower petals with a small touch of red near the base. The nearest comparison cultivars known to the inventor are: 'Coral Reef' U.S. Plant Pat. No. 19,660, 'Pomegranate Kiss' U.S. Plant Pat. No. 21,895, 'Black Cherry Wild' U.S. Plant Pat. No. 21,893 and 'Black Cherry Frost' U.S. Plant Pat. No. 28,605. The flower of 'Coral Reef' is primarily a lighter reddish coral color and it has fewer petals than the new plant. Compared with 'Pomegranate Kiss', the new plant has a more uniform and wider, light-pink, picotee margin and more petals per flower. Compared with 'Black Cherry Wild', the new plant has larger flowers with more petals. Compared with 'Black Cherry Frost', the new plant has more petals, larger flowers and the picotee margin is lighter pink.

*Dianthus* 'Cherry Vanilla' is distinct from its parents and all other *Dianthus* known to the applicant in the following combined traits:

1. Fully-double flowers opening up with a full and rounded face.

2. Petals having a velvety red coloration with faint speckling of medium pink.
3. Petal margin of very light pink.
4. Multiple flowers per stiff, upright peduncle.
5. Large flower size producing a lightly-sweet spicy fragrance.
6. Flower coverage top to bottom of clump, vigorous, with compact habit and finely-textured gray-green foliage.

BRIEF DESCRIPTION OF THE DRAWINGS

The photographs of the new invention are of a two-year-old plant grown in full-sun trial garden and demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
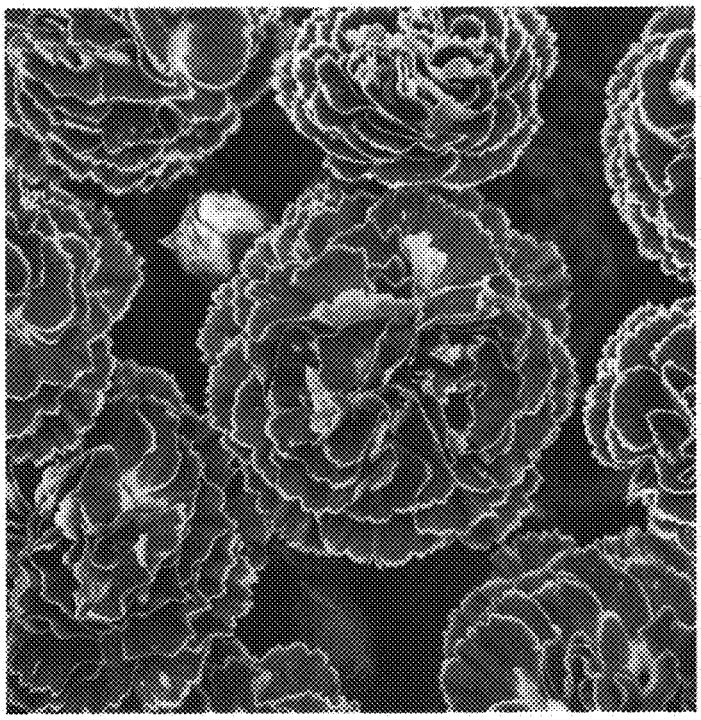
FIG. 1 s a close-up of the flowers and buds.
Figure 2:
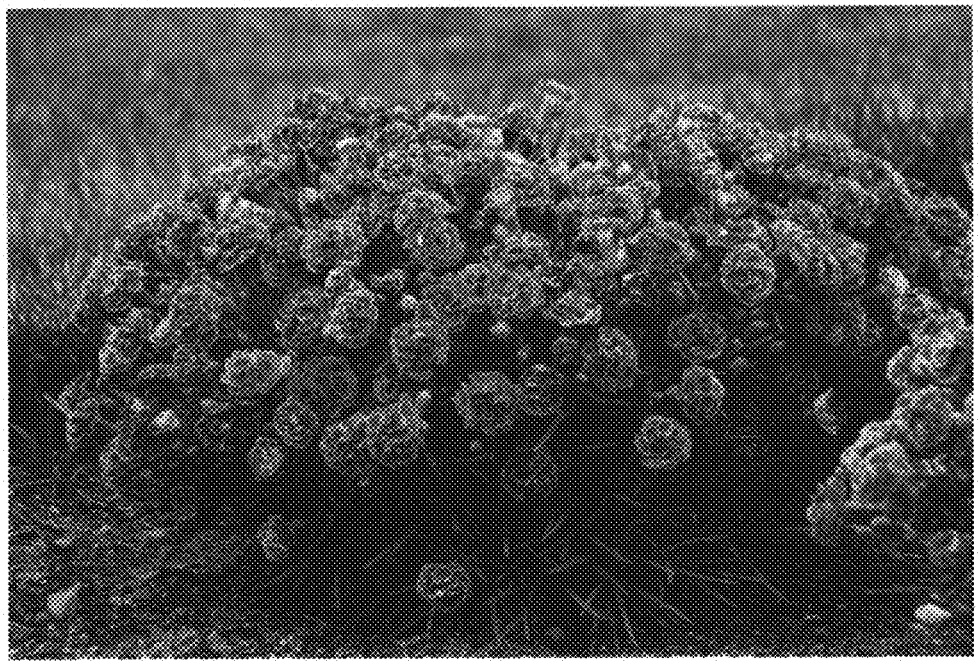
FIG. 2 shows the habit of the plant in mid-season flowering.

The following detailed description of the new plant is based on observations of one-year-old plants in greenhouse-grown containers in addition to two-year-old plants in full-sun trial garden at a nursery in Zeeland, Mich. with supplemental watering, light additions of fertilizer and free of other plant growth regulators. All color usage is in accordance with the 2001 edition of The Royal Horticultural Colour Chart except where common dictionary terms axe used.

Botanical classification: *Dianthus* hybrid;

Parentage: 'WP Passion' as the female or seed parent and 'Fancy Knickers' as the male or pollen parent;

Plant habit: Caespitose, herbaceous, evergreen, winter-hardy perennial; stems and peduncles branched, mostly erect stems; height of foliage about 13.0 cm and about 24.0 cm across; height in flower is about 17.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, strongly glaucous to pruinose both adaxial and abaxial; margin entire to microscopically serrulate; acute apex; base decurrent, adpressed along stem and slightly perfoliate; no fragrance detected; curvature absent; cross section in longitudinal center nearly flat.

*Leaf dimensions*.—To about 9.0 cm long and about 4.5 mm wide, average about 7.5 cm long and 4.0 mm wide.

*Leaf color*.—Young expanding leaves abaxial nearest RHS N138B and adaxial between RHS N138B and RHS 138A; mature adaxial and abaxial blend between RHS N138A and RHS 122A.

*Venation*.—Not pronounced; obscurely pinnate, coloration same as that of leaf top and bottom.

Stems: Upright; terete, glabrous, glaucous, branching at alternate nodes; solid; about 22 stems per plant;

*Stem size*.—About 3.0 cm long to peduncle and about 4.0 mm wide at base.

*Stem color*.—Nearest RHS 122A.

*Branching*.—Numerous; typically alternate, from upper and lower nodes; about 10 per main stem and about 220 per plant; branch size average about 3.0 cm at time of initial flowering.

*Nodes*.—About 3.0 mm across; color nearest RHS 145D.

Internodes: about 11 per stem before peduncle; average about 5.0 mm apart depending on growing temperature, shorter in cooler conditions; thickness medium;

Inflorescence:

*Type*.—Terminal, cymose; perfect; salverform; actinomophic; double.

*Attitude*.—Upright to slightly outward around perimeter of plant.

*Dimension*.—About 4.8 cm across and extending about 4.0 cm above base of calyx tube.

*Flowers per stem*.—Average three.

*Pedicel*.—Glaucous, glabrous, terete, stiff.

*Pedicel size*.—Terminal flower about 2.0 mm long and about 2.0 mm diameter; other flowers average about 5.0 mm long and 1.5 mm diameter.

*Pedicel color*.—Nearest RHS 138B.

*Flower bud*.—Slowly opening; glabrous; glaucous; with calyx still closed: ellipsoid with rounded base and acute apex, about 2.2 cm long and 1.0 cm across at distal fusion point of sepals; with petals extended beyond calyx and still parallel to calyx side: terete, with rounded base and truncate apex or petal tops, about 3.1 cm long and 1.1 cm across at distal fusion point of sepals.

*Flower bud color*.—With petals enclosed in calyx distally nearest RHS 137B and proximally between RHS 144A and RHS N144C; with petals extended beyond calyx petal portion proximally lighter than RHS 155D, distally nearest RHS 62D with blush of RHS 61A.

*Flower period*.—Beginning late spring and continuing for up to six weeks; individual flowers effective about 7 to 10 days.

*Flower fragrance*.—Light, sweet spicy, clove-like.

*Flower lasting quality*.—About six to ten days on or cut from plant.

*Petals*.—Glabrous; up to about 66 per flower; consisting of a rounded blade or limb and a claw; limb and claw combined are flabellate; apex and margin with fine, irregular, shallow dentations typically between 0.5 mm to 1.0 mm deep; limb bent outwardly in distal 15.0 mm to nearly a ninety degree angle creating a full rounded face; limb to about 20.0 mm across, average about 17.0 mm across; claw tapering to attenuate base about 0.3 mm across; whole petal to about 37.0 mm long, average about 34.0 mm long; persistent; undulations typically weak in outer petals and weak to folded in inner petals.

*Petal color*.—Abaxial claw base nearest RHS 145D, mid-claw nearest RHS 145C, distal claw lighter than RHS N155B; abaxial limb base lighter than RHS N155B, distal limb blend between RHS 61A and RHS 60C with white overtone, distal margin nearest RHS 62C; adaxial claw base nearest RHS 155A, mid-claw nearest RHS 145D, distal claw nearest RHS NN155B; adaxial limb main portion blend between RHS 60A and RHS 59B, limb margin nearest RHS 62C and minute speckles in main portion between RHS 63C and RHS 64D, and limb base nearest RHS N155B.

*Petal dimension*.—Overall to about 37.0 cm long, average about 35.0 mm long; to about 20.0 mm across at widest portion of limb, average about 17.0 mm across; claw to about 0.3 m wide at base and about 22.0 mm long, average about 22.0 mm long; lighter colored limb margin about 1.2 mm wide and speckles in main limb portion average 1.0 mm diameter.

*Calyx*.—Glabrous; glaucous abaxial; margins entire to micro-puberulent; consisting of five sepals with acute apex and fused base forming five-toothed corolla tube fused in about proximal 16.0 mm; individually about 20.0 mm long and about 9.0 mm across at distal fusion; campanulate to about 20.0 mm long and about 13.0 mm in diameter at apex.

*Calyx color*.—Abaxial distal portion nearest RHS 135A and proximally nearest RHS 144B with marginal 1.0 mm translucent to nearest RHS 161D and nearest RHS 165C at the apex; adaxial basal two-thirds lighter than RHS 138D, apical one-third nearest RHS 138B and margin translucent to nearest 161D and nearest RHS 165C at apex.

*Peduncle*.—Glabrous, glaucous, terete, stiff; about 10.0 cm long and about 3.0 mm diameter at base; attitude mostly upright.

*Peduncle color*.—Nearest RHS 122A.

*Epicalyx*.—Two pairs; opposite, glaucous, glabrous; sessile, margin entire, broadly lanceolate with broadly acute apex and cuneate base; outer pair about 10.0 mm long and about 7.0 mm wide, inner pair about 8.5 mm long and about 6.5 mm across.

*Epicalyx color*.—Both pairs abaxial and adaxial distal portion nearest RHS 135A and proximally between RHS 138A and RHS 138B, margin translucent to nearest RHS 145D.

*Androecium*.—Variable number between zero and seven stamens, typically not all fully formed, to some staminode petals or without anther. Filaments: when present to about 22.0 mm long, about 0.5 mm diameter; color white, lighter than RHS 155D. Anther: when present oblong, dorsifixed; about 2.5 mm long and about 0.7 mm wide; color with longitudinal portions nearest RHS 198C and RHS201A. Pollen: not observed.

*Gynoecium*.—Single. Style: trifurcate just above ovary; glabrous abaxial and becoming puberulent in adaxial distal one-third. Pistil: adaxial puberulent, glabrous abaxial; distally curved over 360 degrees in distal 10.0 mm; about 30.0 mm long and 1.0 mm diameter; color proximally and abaxial white, lighter than RHS 155D, and distally becoming nearest RHS 64A on adaxial side. Stigma: slightly flattened abaxial to adaxial; puberulent; about 1.0 cm long and 1.0 mm wide; color nearest RHS 64A. Ovary: superior; ellipsoid-shaped with broadly acute apex and truncate base; about 8.0 mm long and 5.0 mm wide; surface smooth; color nearest RHS 145B distally and RHS 4D proximally.

Fruit and seed: Not observed; possibly sterile or recalcitrant;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Cherry Vanilla' essentially as herein described and illustrated.

* * * * *